(12) United States Patent
Penner et al.

(10) Patent No.: US 8,070,930 B2
(45) Date of Patent: Dec. 6, 2011

(54) METHODS FOR FABRICATING METAL NANOWIRES

(75) Inventors: Reginald Mark Penner, Laguna Beach, CA (US); Michael Paul Zach, Irvine, CA (US); Fred Favier, Saint Clemente de Riviere (FR)

(73) Assignee: The Regents of the University of California, Oakland, CA (US)

( * ) Notice: Subject to any disclaimer, the term of this patent is extended or adjusted under 35 U.S.C. 154(b) by 506 days.

(21) Appl. No.: 11/742,223

(22) Filed: Apr. 30, 2007

(65) Prior Publication Data
US 2008/0128284 A1 Jun. 5, 2008

Related U.S. Application Data (63) Continuation of application No. 10/861,821, filed on Jun. 3, 2004, now Pat. No. 7,220,346, which is a continuation of application No. 09/976,990, filed on Oct. 12, 2002, now Pat. No. 6,843,902.

(60) Provisional application No. 60/306,715, filed on Jul. 20, 2001, provisional application No. 60/317,862, filed on Sep. 5, 2001.

(51) Int. Cl.
*C25D 5/02* (2006.01)
(52) U.S. Cl. .................................. 205/118; 205/125
(58) Field of Classification Search ............. 205/118, 205/122, 136, 170, 125
See application file for complete search history.

(56) References Cited

U.S. PATENT DOCUMENTS

| 6,172,902 | B1 | 1/2001 | Wegrowe et al. |
| 6,476,409 | B2 | 11/2002 | Iwasaki et al. |
| 6,843,902 | B1 * | 1/2005 | Penner et al. ............ 205/76 |
| 7,220,346 | B2 * | 5/2007 | Penner et al. ............ 205/76 |

OTHER PUBLICATIONS

Kovtyukhova et al. ("Layer-by-Layer Assembly of Rectifying Junctions in and on Metal Nanowires," J. Phys. Chem. B, 2001, 105 (37), pp. 8762-8769, published Aug. 14, 2001).*
Heydon et al. ("Magnetic properties of electrodeposited nanowires," J. Phys. D: Appl. Phys. 30, 1083, 1997).*
Lowenheim (Electroplating, pp. 137-139, 1978).*
Zach et al. ("Molybdenum Nanowires by Electrodeposition", Science 290, 2000, 2120).*

(Continued)

*Primary Examiner* — Luan Van
(74) *Attorney, Agent, or Firm* — Orrick, Herrington & Sutcliffe LLP (57) ABSTRACT

Methods for the preparation of long, dimensionally uniform, metallic nanowires that are removable from the surface on which they are synthesized. The methods include the selective electrodeposition of metal nanowires at step edges present on a stepped surface, such as graphite, from an aqueous solution containing a metal or metal oxide. Where a metal oxide is first deposited, the metal oxide nanowires are reduced via a gas phase reduction at elevated temperatures to metal nanowires. Alternatively, beaded or hybrid nanowires comprising a metal A into which nanoparticles of a metal B have been inserted may be prepared by first electrodepositing nanoparticles of metal B selectively along step edges of a stepped surface, capping these nanoparticles with a molecular layer of an organic ligand, selectively electrodepositing nanowire segments of metal A between nanoparticles of metal B and then heating the surface of the hybrid nanowire under reducing conditions to remove the ligand layer. In all three methods, the nanowires may be removed from the stepped surface by embedding the wires in a polymer film, and then peeling this film containing the embedded wires off of the stepped surface.

8 Claims, 8 Drawing Sheets

OTHER PUBLICATIONS

L. Escapa and N. Garcia, "Is the Observed Quantized Conductance on Small Contacts Due to Coherent Ballistic Transport", App. Phys. Lett. 56 (1990) 901-903.

J. L. Costa Kramer, N. Garcia and H. Olin, "Conductance quantization in bismuth nanowires at 4 K", Phys. Rev. Lett. 78 (1997) 4990-4993.

Z. B. Zhang, X. Z. Sun, M. S. Dresselhaus, J. Y. Ying and J. Heremans, "Electronic transport properties of single-crystal bismuth nanowire arrays", Phys. Rev. B 61 (2000) 4850-4861.

Z. B. Zhang, X. Z. Sun, M. S. Dresselhaus, J. Y. Ying and J. P. Heremans, "Mag netotransport investigations of ultrafine single-crystalline bismuth nanowire arrays", App. Phys. Lett. 73 (1998) 1589-1591.

J. I. Pascual, J. Mendez, J. Gomezherrero, A. M. Baro, N. Garcia and V. T. Binh, "Quantum Contact in Gold Nanostructures by Scanning Tunneling Microscopy", Phys. Rev. Lett. 71 (1993) 1852-1855.

J. I. Pascual, J. Mendez, J. Gomezherrero, A. M. Baro, N. Garcia, U. Landman, W. D. Leudtke, E. N. Bogachek and H. P. Cheng, "Electrical and Mechanical Properties of Metallic Nanowires—Conductance Quantization and Localization", J.Vac. Sci. Technol. B 13 (1995) 1280-1284.

J. Heremans, C. M. Thrush, Z. Zhang, X. Sun, M. S. Dresselhaus, J. Y. Ying and D. T. Morelli, "Magnetoresistance of bismuth nanowire arrays: A possible transition from one-dimensional to three-dimensional localization", Phys. Rev. B 58 (1998) 10091-10095.

E. N. Bogachek, A. G. Scherbakov and U. Landman, "Magnetic Switching and Thermal Enhancement of Quantum Transport Through Nanowires", Phys. Rev. B 53 (1996) 13246-1 3249.

E. N. Bogachek, A. G. Scherbakov and U. Landman, "Nonlinear magnetoconductance of nanowires", Phys. Rev. B 56 (1997) 14917-14920.

Liu, C. L. Chien, P. C. Searson and Y. Z. Kui, "Structural and magneto-transport properties of electrodeposited bismuth nanowires", App. Phys. Lefl. 73 (1998) 1436-1438.

K. Liu, K. Nagodawithana, P. C. Searson and C. L. Chien, "Perpendicular Giant Magnetoresistance of Multilayered Co/Cu Nanowires", Phys. Rev. B 51 (1995) 7381-7384.

K. Liu, C. L. Chien and P. C. Searson, "Finite-size effects in bismuth nanowires", Phys. Rev. B 58 (1998) R14681-R14684.

U. Landman, W. D. Luedtke, B. E. Salisbury and R. L. Whetten, "Reversible Manipulations of Room Temperature Mechanical and Quantum Transport Properties in Nanowire Junctions", Phys. Rev. Lett. 77 (1996) 1362-1 365.

C. Yannouleas and U. Landman, "On mesoscopic forces and quantized conductance in model metallic nanowires", J. Phys. Chem. B 101 (1997) 5780-5783.

H. Ikeda, Y. Qi, T. Cagin, K. Samwer, W. L. Johnson and W. A. Goddard, "Strain rate induced amorphization in metallic nanowires", Phys. Rev. Lefl. 82 (1999) 2900-2903.

Blom, H. Olin, J. L. CostaKramer, N. Garcia, M. Jonson, P. A. Serena and R. I. Shekhter, "Free-electron model for mesoscopic force fluctuations in nanowires", Phys. Rev. B 57 (1998) 8830-8833.

H. Haldcinen, R. N. Barnett and U. Langman, "Gold Nanowire and Their Chemical Modifications", J. Phys. Chem. B 103 (1999) 8814.

C. Z. Li, H. X. He, A. Bogozi, J. S. Bunch and N. J. Tao, "Molecular Detection based on Conductance Quantization of Nanowires.", App. Phys. Lett. 76 (2000) 1333.

M. P. Zach, K. Ng and R. M. Penner, "Molybdenum Nanowires by Electrodeposition", Science 290 (2000) 2120.

D. Y. Petrovykh, F. J. Himpsel and T. Jung, "Width distribution of nanowires grown by step decoration", Surf. Sci. 407 (1998) 189-1 99.

S. Morin, A. Lachenwitzer, O. M. Magnussen and R. J. Behm, "Potential-controlled step flow to 3D step decoration transition: Ni electrodeposition on Ag (1 11)", Phys. Rev. Lett. 83 (1999) 5066-5069.

E. A. Abd El Meguid, P. Berenz and H. Baltruschat, "Step decoration at Pt single crystal electrodes: role of the anion", J. Electroanal. Chem. 467 (1999) 50-59.

J. Dekoster, B. Degroote, H. Pattyn, G. Langouche, A. Vantomme and S. Degroote, "Step decoration during deposition of Co on Ag(001) by ultralow energy ion beams", App. Phys. Lett. 75 (1999) 938-940.

R. K. Kawakami, M. O. Bowen, H. J. Choi, E. J. Escorcia-Aparicio and Z. Q. Qiu, "Step-induced magnetic anisotropy in Co stepped Cu(001) as a function of step density and Cu step decoration", J. Appl. Phys. 85 (1999) 4955-4957.

M. Blanc, K. Kuhnke, V. Marsico and K. Kern, "Probing step decoration by grazing-incidence helium scattering", Surf. Sci. 414 (1998) L964-L969.

P. Gambardella, M. Blanc, H. Brune, K. Kuhnke and K. Kern, "One-dimensional metal chains on Pt vicinal surfaces", Phys. Rev. B 61 (2000) 2254-2262.

A. Dallmeyer, C. Carbone, W. Eberhardt, C. Pampuch, O. Rader, W. Gudat, P. Gambardella and K. Kern, "Electronic states and magnetism of monatomic Co and Cu wires", Phys. Rev. B 61 (2000) R5133-R51 36.

E. Braun, Y. Eichen, U. Sivan and G. BenYoseph, "DNA-templated assembly and electrode attachment of a conducting silver wire", Nature 391 (1998) 775-778.

Y. Eichen, E. Braun, U. Sivan and G. BenYoseph, "Self-assembly of nanoelectronic components and circuits using biological templates", Acta Polymerica 49 (1998) 663-670.

G. Fasol and K. Runge, "Selective electrodeposition of nanometer scale magnetic wires", App. Phys. Lett. 70 (1997) 2467-2468.

C. W. Zhou, J. Kong and H. J. Dai, "Electrical measurements of individual semiconducting single-walled carbon nanotubes of various diameters", App. Phys. Lett. 76 (2000) 1597-1 599.

A. A. Setlur, J. M. Lauerhaus, J.-Y. Dai and R. P. H. Chang, "A Method for Synthesizing Lage Quantities of Carbon Nanotubes and Encapsulated copper nanowires", APL 69 (1996) 345.

W. K. Hsu, S. Trasobares, H. Terrones, M. Terrones, N. Grobert, Y. Q. Zhu, W. Z. Li, R. Escudero, J. P. Hare, H. W. Kroto and D. R. M. Walton, "Electrolytic formation of carbon-sheathed mixed Sn-Pb nanowires", Chem. Mat. 11 (1999) 1747-1751.

W. K. Hsu, J. Li, H. Terrones, M. Terrones, N. Grobert, Y. Q. Zhu, S. Trasobares, J. P. Hare, C. J. Pickett, H. W. Kroto and D. R. M. Walton, "Electrochemical production of low-melting metal nanowires", Chem. Phys. Lett. 301 (1999) 159-166.

W. K. Hsu, M. Terrones, H. Terrones, N. Groben, A. I. Kirkland, J. P. Hare, K. Prassides, P. D. Townsend, H. W. Kroto and D. R. M. Walton, "Electrochemical formation of novel nanowires and their dynamic effects", Chem. Phys. Lett. 284 (1998) 177-183.

M. Terrones, W. K. Hsu, A. Schilder, H. Terrones, N. Grobert, J. P. Hare, Y. Q. Zhu, M. Schwoerer, K. Prassides, H. W. Kroto and D. R. M. Walton, "Novel nanotubes and encapsulated nanowires", Appl. Phys. A 66 (1998) 307-317.

N. Demoncy, O. Stephan, N. Brun, C. Colliex, A. Loiseau and H. Pascard, "Filling carbon nanotubes with metals by the arc-discharge method: the key role of sulfur", European Physical Journal B 4 (1998) 147-157.

N. Demoncy, O. Stephan, N. Brun, C. Colliex, A. Loiseau and H. Pascard, "Sulfur: the key for filling carbon nanotubes with metals", Synth. Met. 103 (1999) 2380-2383.

T. Bjornholm, T. Hassenkam, D. R. Greve, R. D. McCullough, M. Jayaraman, S. M. Savoy, C. E. Jones and J. T. McDevitt, "Polythiophene nanowires", Adv. Mat. 11 (1999) 1218-1221.

D. A. Tulchinsky, M. H. Kelley, J. J. McClelland, R. Gupta and R. J. Celotta, "Fabrication and domain imaging of iron magnetic nanowire arrays", Journal of Vacuum Science & Technology a-Vacuum Surfaces and Films 16 (1998) 1817-1819.

W. R. Anderson, C. C. Bradley, J. J. McClelland and R. J. Celotta, "Minimizing feature width in atom optically fabricated chromium nanostructures", Physical Review A 59 (1999) 2476-2485.

R. J. Celotta, R. Gupta, R. E. Scholten and J. J. McClelland, "Nanostructure Fabrication Via Laser-Focused Atomic Deposition", J. Appl. Phys. 79 (1996) 6079-6083.

E. Jurdik, T. Rasing, H. van Kempen, C. C. Bradley and J. J. McClelland, "Surface growth in laser-focused atomic deposition", Phys. Rev. B 60 (1999) 1543-1546.

N. Agrait, G. Rubio and S. Vieira, "Plastic Deformation of Nanometer-Scale Gold Connective Necks", Phys. Rev. Lett. 74 (1995) 3995-3998.

G. Rubio, N. Agrait and S. Vieira, "Atomic-Sized Metallic Contacts—Mechanical Properties and Electronic Transport", Phys. Rev. Lett. 76 (1996) 2302-2305.

J. Jorritsma, M. A. M. Gijs, J. M. Kerkhof and J. G. H. Stienen, "General Technique for Fabricating Large Arrays of Nanowires", Nanotechnology 7 (1996) 263-265.

J. Jorritsma, M. A. M. Gijs, C. Schonenberger and J. G. H. Stienen, "Fabrication of Large Arrays of Metallic Nanowires on V-Grooved Substrates", App. Phys. Lett. 67 (1995) 1489-1491.

S. A. Sapp, D. T. Mitchell and C. R. Martin, "Using template-synthesized micro and nanowires as building blocks for self-assembly of supramolecular architectures", Chem. Mat. 11 (1999) 1183-1185, 1185A.

C R. Martin, D. J. Dermody, B. D. Reiss, M. M. Fang, L. A. Lyon, M. J. Natan and T. E. Mallouk, "Orthogonal self-assembly on colloidal gold-platinum nanorods", Adv. Mat. 11 (1999) 1021-1025.

B. A. Korgel and D. Fitzmaurice, "Self-assembly of silver nanocrystals into two-dimensional nanowire arrays", Adv. Mat. 10 (1998) 661-665.

L. C. Brousseau, J. P. Novak, S. M. Marinakos and D. L. Feldheim, "Assembly of phenylacetylene-bridged gold nanocluster dimers and timers", Adv. Mat. 11 (1999) 447-449,427.

Y. Zhou, S. H. Yu, X. P. Cui, C. Y. Wang and Z. Y. Chen, "Formation of Silver Nanowires by a Novel Solid-Liquid Phase Arc Dicharge Method", Chem. Mat. 11 (1999) 545.

G. L. G. L. Hornyak, C. J. Patrissi and C. R. Martin, "Finite sized oblate and orthoprolate metal nanoparticles: Optical theory and potential as surface enhanced Raman spectroscopic substrates", Nanostructured Materials 9 (1997) 705-708.

D. N. Davydov, J. Haruyama, D. Routkevitch, B. W. Statt, D. Ellis, M. Moskovits and J. M. Xu, "Nonlithographic nanowire-array tunnel device: Fabrication, zerobias anomalies, and Coulomb blockade", Phys. Rev. B 57 (1998) 13550-1 3553.

J. Muster, G. T. Kim, V. Krstic, J. G. Park, Y. W. Park, S. Roth and M. Burghard, "Electrical transport through individual vanadium pentoxide nanowires", Adv. Mat. 12 (2000) 420-424, 398.

G. T. Kim, J. Muster, V. Krstic, J. G. Park, Y. W. Park, S. Roth and M. Burghard, "Field-effect transistor made of individual V205 nanofibers", App. Phys. Lett. 76 (2000) 1875-1 877.

Jung, Y. W. Mo and F. J. Himpsel, "Identification of Metals in Scanning Tunneling Microscopy Via Image States", Phys. Rev. Lett. 74 (1995) 1641 -1 644.

J. Fransaer and R. M. Penner, "Brown Dynamics Simulations of the Growth of metal Nanocrystal Ensembles on Electrodes Surfaces From Solution. I. Instantaneous Nucleation and Diffusion-Controlled Growth", J. Phys. Chem. B 103 (1999) 7643.

Ng, H. Liu and R. M. Penner, Langmuir 16 (2000) 4016.

C. Durkan and M. E. Welland, "Size effects in the electrical resistivity of polycrystalline nanowires", Phys. Rev. B 61 (2000) 14215-14218.

Brumlik et al., "Template synthesis of metal microtuble ensembles utilizing chemical, electrochemical, and vacuum deposition techniques", J. Mater. Res., vol. 9, No. 5 (1996) 1174.

Preston et al., "Optical Characterization of Anodic Aluminum Oxide Films Containing Electrochemically Deposited Metal Particles", J. Phys. Chem. 97 (1993) 8495-8503.

Routkevitch et al., "Electrochemical Fabrication of CdS Nanowire Arrays in Porous Anodic Aluminum Oxide", J. Phys. Chem. 100 (1996) 14037-14047.

Sun et al., "Finite-size effects in nickel nanowire arrays", Phys. Rev. B, vol. 61, No. 10 (2000) R6464-R6466.

P.C. Searson et al., "Electrochemical processing of metallic nanowire arrays and nanocomposites", J. Elec. Mater., vol. 24, No. 8 (1995) 955-960.

L. Sun et al., "Electrochemicl deposition of nickel nanowire arrays in single-crystal mica films", Appl. Phys. Ltrs., vol. 74, No. 19 (1999) 2803-2805.

Zach et al., "Nanocrystalline nickel nanoparticles", Adv. Mater., vol. 12, No. 12 (2000) 878-883.

Zoval et al., "Electrochemical preparation of platinum nanocrystal-lites with size selectivity on basal plane oriented graphite surfaces", J. Phys. Chem. B 102 (1998) 1166-1175.

Himpsel et al., "Nanowires by step decoration", MRS Bulletin (Aug. 1999) 20-24.

Noll et al., "Template electropolymerization of polypyrrole nanostructures on highly ordered pyrolytic graphite step and pit defects", J. Electrochem. Socl., vol. 145, No. 10 (1998) 3320-3328.

Martin, "Template synthesis of polymeric and metal microtubules", Adv. Mater. 3, No. 9 (1999) 457-459.

C. A. Foss, G. L. Hornyak, J. A. Stockert and C. R. Martin, "Template-Synthesized Nanoscopic Gold Particles—Optical Spectroscopy and the Effects of Particle Size and Shape", J. Phys. Chem. 98 (1994) 2963.

C. A. Foss, M. J. Tierney and C. R. Martin, "Template Synthesis of Infrared-Transparent Metal Microcylinders: Comparison of Optical Properties With the Predictions of Effective Medium Theory", J. Phys. Chem. 96 (1992) 9001-9007.

C. J. Brumlik, V. P. Menon and C. R. Martin, "Template Synthesis of Metal Microtubule Ensembles Utilizing Chemical, Electrochemical, and Vacuum Deposition Techniques", J. Mat. Res. 9 (1994) 1174.

Routkevitch, T. Bigioni, M. Moskovits and J. M. Xu, "Electrochemical Fabrication of Cds Nanowire Arrays in Porous Anodic Aluminum Oxide Templates", J. Phys. Chem. 100 (1996) 14037-14047.

F. J. Himpsel, T. Jung and J. E. Ortega, "Nanowires on stepped metal surfaces", Surface Review and Letters 4 (1997) 371-380.

S. Strbac et al., "Nanoscale pattern formation during electrodeposition: Ru on reconstructed Au(111)", Phy. Rev. Ltrs., vol. 83, No. 16 (1999) 3246-3249.

J. I. Pascual, J. Mendez, J. Gomezherrero, A. M. Baro, N. Garcia, U. Landman, W. D. Luedtke, E. N. Bogachek and H. P. Cheng, "Properties of Metallic Nanowires—From Conductance Quantization to Localization", Science 267 (1995) 1793-1 795.

H. J. Dai, "Probing Electrical Transport in Nanomaterials—Conductivity of Individual Carbon Nanotubes (vol. 272, p. 523, 1996)", Science 272 (1996) 1861-1861.

M. Terrones, N. Grobert, W. K. Hsu, Y. Q. Zhu, W. B. Hu, H. Terrones, J. P. Hare, H. W. Kroto and D. R. M. Walton, "Advances in the creation of filled nanotubes and novel nanowires", MRS Bulletin 24 (1999) 43-49.

C. Guerretpiecourt, Y. Lebouar, A. Loiseau and H. Pascard, "Relation Between Metal Electronic Structure and Morphology of Metal Compounds Inside Carbon Nanotubes", Nature 372 (1994) 761-765.

A. Loiseau and H. Pascard, "Synthesis of Long Carbon Nanotubes Filled With Se, S, Sb and Ge by the Arc Method", Chem. Phys. Lett. 256 (1996) 246-252.

B. K. Pradhan, T. Kyotani and A. Tomita, "Nickel nanowires of 4 nm diameter in the cavity of carbon nanotubes", Chem. Comm. (1999) 1317-1318.

J. Sloan, D. M. Wright, H. G. Woo, S. Bailey, G. Brown, A. P. E. York, K. S. Coleman, J. L. Hutchison and M. L. H. Green, "Capillarity and silver nanowire formation observed in single walled carbon nanotubes", Chem. Comm. (1999) 699-700.

R. E. Scholten, J. J. McClelland, E. C. Palm, A. Gavrin and R. J. Celotta, "Nanostructure Fabrication Via Direct Writing With Atoms Focused in Laser Fields", J. Vac. Sci. Technol. B 12 (1994) 1847-1 850.

R. Gupta, J. J. McClelland, Z. J. Jabbour and R. J. Celotta, "Nanofabrication of a Two-Dimensional Array Using Laser-Focused Atomic Deposition", App. Phys. Lett. 67 (1995) 1378-1380.

J. M. Krans, J. M. Vanruitenbeek, V. V. Fisun, I. K. Yanson and L. J. Dejongh, "The Signature of Conductance Quantization in Metallic Point Contacts", Nature 375 (1995) 767-769.

C. J. Muller, J. M. Krans, T. N. Todorov and M. A. Reed, "Quantization Effects in the Conductance of Metallic Contacts at Room Temperature", Phys. Rev. B 53 (1996) 1022-1025.

J. M. Krans, C. J. Muller, I. K. Yanson, T. C. M. Govaert, R. Hesper and J. M. Vanruitenbeek, "One-Atom Point Contacts", Phys. Rev. B 48 (1993) 14721-14724.

J. A. Tones, J. I. Pascual and J. J. Saenz, "Theory of Conduction Through Narrow Constrictions in a 3-Dimensional Electron Gas", Phys. Rev. B 49 (1994) 16581-16584.

C. J. Brumlik and C. R. Martin, "Template Synthesis of Metal Microtubules", J. Am. Chem. Soc. 113 (1991) 3174-3175.

J. Clavilier, J. M. Feliu and A. Aldaz J. Electroanal. Chem. 243 (1988) 419-433.

M. Aktary, C. E. Lee, Y. Xing, S. H. Bergens and M. T. McDermott, "Surface-directed deposition of platinum nanostructures on graphite by chemical vapor deposition", Langmuir 16 (2000) 5837-5840.

S. J. Tans, M. H. Devoret, H. J. Dai, A. Thess, R. E. Smalley, L. J. Geerligs and C. Dekker, "Individual single-wall carbon nanotubes as quantum wires", Nature 386 (1997) 474-477.

E. H. Sondheimer,, Adv. Phys. 1, No. 1 (1952) 1-42.

A. F. Mayadas, M. Shatzkes and M. Janak,, Appl. Phys. Lett. 14 (1969) 345.

A. F. Mayadas and M. Shatzkes,, Phys. Rev. B 1 (1970) 1382.

M. Terrones, W. K. Hsu, A. Schilder, H. Terrones, N. Grobert, J. P. Hare, Y. Q. Zhu, M. Schwoerer, K. Prassides, H. W. Kroto and D. R. M. Walton, "Novel nanotubes and encapsulated nanowires", Appl. Phys. A 66 (1998) 307-317.

R. J. Nichols, D. M. Kolb and R. J. Behm, "STM Observations of the Initial Stages of Copper Deposition on Gold Single Crystal Electrodes", J. Electroanal. Chem. 313 (1991) 109.

T. Jung, R. Schlittler, J. K. Gimzewski and F. J. Himpsel, "One-Dimensional Metal Structures at Decorated Steps", Appl. Phys. A 61 (1995) 467-474.

Y. W. Mo and F. J. Himpsel, "Spectroscopic signature of Cu on W(1 10) From Scanning . . . ", Phys. Rev. B 50 (1994) 7868.

K. Fuchs et al., "The Conductivity of Thin Metallic Films According to the Electron Theory of Metals", Proc. Cambridge Philos. Soc. 34 (1938) 100-108.

Blanc et al., "Probing step decoration by grazing-incidence helium scattering", Surf. Sci. 414 (1998) L964-L969.

Gambardella et al., "One-dimensional metal chains on Pt vicinal surfaces", Phys. Rev. B 61, No. 3 (2000) 2254-2262.

Dallmeyer et al., "Electronic states and magnetism of monatomic Co and Cu wires", Phys. Rev. B 61, No. 8 (2000) R5133-R5136.

Sharp et al., "Using template-synthesized micro- and nanowires as building blocks for self-assembly of supramolecular architectures", Chem. Mat. 11, No. 5 (1999) 1183-1185.

Hornyak et al., "Finite sized oblate and ortho-prolate metal nanoparticles: optical theory and potential as surface enhanced reman spectroscopic substrates", Nanostructured Materials, vol. 9 (1997) 705-708.

Brumlik and Martin, "Template synthesis of metal microtubules", J. Am. Chem. Soc. 113 (1991) 3174-3175.

Penner, R.M., "Hybrid electrochemical/chemical synthesis of quantum dots", Acc. Chem. Res. 33 (2000) 78-86.

Whitney et al., "Fabrication and magnetic properties of arrays of metallic nanowires", Science 261 (1993) 1316-1319.

Bard, A.J., et al., "Electrochemical Methods, Fundamentals and Applications," $2^{nd}$ Ed., Wiley, New York, 2001 (ISBNO-471-04372-9) 35-48.

Vieu et al., "Electron beam lithography: resolution limits and applications", Appl. Surf. Science 164 (2000) 111-117.

* cited by examiner

METHODS FOR FABRICATING METAL NANOWIRES

CROSS-REFERENCE TO RELATED APPLICATION

This application is a continuation of Ser. No. 10/861,821 filed Jun. 3, 2004, now U.S. Pat. No. 7,220,346 which is a continuation of Ser. No. 09/976,990 filed Oct. 12, 2002 which issued as U.S. Pat. No. 6,843,902, which claims priority of Provisional U.S. Patent Application Ser. No. 60/306,715 filed on Jul. 20, 2001 and Provisional U.S. Patent Application Ser. No. 60/317,862, filed on Sep. 5, 2001 which applications are fully incorporated herein by reference.

This invention was made with Government support under contract no. DMR-9876479. The government has certain rights in this invention.

FIELD OF THE INVENTION

The invention relates to metal nanowires and, more particularly, to methods which facilitate the fabrication of long, free standing metal nanowires.

BACKGROUND

Metal nanowires have great potential for immediate use in small electronic circuits, sensitive chemical sensors or any application requiring metal filaments, and will likely be required as interconnects in the nanometer-scale electronics of the future, especially those future electronics which are not based on existing silicon technology. However, there are few methods for preparing nanowires that have such technological utility. More particularly, few methods are capable of producing nanowires that are long (i.e., greater than ten microns in length), uniform in diameter, free standing, and metallic. Two of the most successful approaches have been template synthesis and step-edge decoration.

The template synthesis method, which is described in publications by the research groups of M. Moskovits[16-18], C. R. Martin[8-15], and P. C. Searson[21-27], appears to permit the growth of metal nanowires over a wide range of diameters (from nanometer to micron scale) and for a variety of different metals. Template synthesis involves the growth of carbon, metals, or polymers in the void volumes of a nonconductive porous host such as polycarbonate ultrafiltration membranes, porous $Al_2O_3$ films, and track-etched mica crystals all of which possess long (microns or longer), dimensionally uniform pores. In general, these pores are oriented perpendicular to the plane of the porous film or membrane. Nanowires are produced by filling these pores with a conductive material. Template synthesis, however, is limited by its reliance on a template. Because all of the templates listed above possess linear, cylindrical (or prismatic) pores, only linear nanowires can be produced. Moreover, nanowires produced by template synthesis are limited to a maximum length that is equal to the thickness of the porous host membrane, which tends to range from 0.1 to 20 microns.

The step edge decoration method, which is described in publications by Himpsel[3-4], Kern[5-7], Behm[2] and others, involves the selective deposition of a metal or other material, such as $CaF_2$, at atomic step edges on a vicinal single crystal surface. Step edge decoration can be controlled to yield continuous "wires" of varied width and interwire spacing. Long nanowires that are many microns in length have been prepared. Because the dimension of the "wire" perpendicular to the vicinal surface has usually been limited to one or at most two atomic layers, it has not been possible to remove these ultra thin metallic ribbons from the surfaces on which they are synthesized. The technological utility of such nanowires is necessarily limited as a result.

In view of the foregoing, it would be desirable to provide methods that facilitate the fabrication of nanowires that are metallic, long (i.e., greater than ten microns in length), uniform in diameter, and removable from the surface on which they are synthesized and, thus, free standing.

SUMMARY OF INVENTION

The present invention is directed to methods that facilitate the fabrication of nanowires that are metallic, long (i.e., greater than ten microns in length), uniform in diameter, and removable from the surface on which they are synthesized and, thus, free standing. The fabrication processes of the present invention provide an electrochemical route to dimensionally uniform and mechanically robust metal nanowires that range in diameter from approximately 10-15 nm to approximately 1.0 μm, and are up to approximately 1.0 mm or more in length. The metal nanowires produced by the methods of the present invention advantageously exhibit wire diameter uniformity along the length of the wire as well as from wire-to-wire for thousands of nanowires. Preferably, the relative standard deviation from a mean diameter tends to be in a range of about 5 to 20%, and more preferably is no more than about 10%. In addition, the metal nanowires produced by the methods of the present invention tend to be electrically continuous along their entire length, i.e., typically less than about 5% of the wires produced by the methods of the present invention tend to show any visible breaks.

The present invention includes three interrelated step-decoration methods that are based on the selective electrodeposition of a metal or metal oxide from an aqueous solution at step edges present on a basal plane-oriented surface, such as graphite, that is exposed to the solution. In a first innovative aspect of the present invention (Method I), metal oxide from an aqueous solution is selectively electrodeposited along step edges present on the stepped surface to form precursor metal oxide wires. The metal oxide nucleates at a high linear density along the step edges forming beaded chains of metal oxide nuclei, which, with continued deposition, rapidly grow into a hemicylindrical nanowires. Wire growth involves low overpotential deposition at constant, or nearly constant, deposition current. Once formed, the precursor metal oxide nanowires are preferably reduced in hydrogen gas ($H_2$) at elevated temperatures to produce metal nanowires. Preferably this gas phase reduction occurs at about 500° C. for about an hour.

In a second innovative aspect of the present invention (Method II), metal nanowires are prepared by direct electrodeposition of metal from an aqueous solution along step edges present on a stepped surface exposed to the solution. Following a nucleation pulse, the metal nucleates at a high linear density along the step edges forming beaded chains of metal nuclei, which, with continued deposition, grow into hemicylindrical nanowires. Wire growth involves low overpotential deposition at constant, or nearly constant, low deposition current. The deposition rates according to this method are preferably extremely low, e.g., the deposition rate to prepare a palladium nanowire via direct electrodepositon having a 200 nm diameter was about 10 minutes and a 300 nm diameter was about 20 minutes.

In a third innovative aspect of the present invention (Method III), beaded or hybrid metal nanowires comprising a first metal (metal A) into which nanoparticles of a second metal (metal B) have been inserted are prepared by first electrodepositing nanoparticles of metal B selectively along step edges of a step surface. The metal B nanoparticles are then capped with a molecular layer of an organic ligand having a strong affinity for the surface of the metal B nanoparticles. Metal A is then selectively electrodeposited along the step edges separating each metal B nanoparticle according to Method I or II. The ligand layer is preferably removed by heating the surface under reducing conditions in order to retain the metallic composition of the particles and connecting nanowire segments. The nanoparticles incorporated into the nanowires may range in diameter from the diameter of the nanowire itself, e.g., as small as about 10 nm, to about 1.0 µm or more.

In all three methods, the nanowires may be removed from the graphite surface by embedding the wires in a polymer film, and then pealing this film containing the embedded nanowires off of the graphite surface. This removal step makes the nanowires available for electrical characterization, for use as interconnects for connecting two nanometer-scale elements of a circuit, for the implementation of a variety of nanowire-based devices including sensors and biosensors, and for wiring of semiconductor quantum dots[20] to form a circuit. When used in sensors, the binding of an analyte molecule to the surface of the nanowire induces a measurable change in the nanowire conductivity.

Other objects and features of the present invention will become apparent from consideration of the following description taken in conjunction with the accompanying drawings.

DESCRIPTION

Referring in detail to the figures, methods that facilitate the fabrication of metallic nanowires and metallic nanowires prepared in accordance with the methods of the present invention are shown. The methods of the present invention involve fabrication processes that provide an electrochemical route to dimensionally uniform, mechanically robust, long metal nanowires that are removable from the surface on which they are synthesized and, thus, free standing. The metal nanowires produced by the methods of the present invention tend to range in diameter from approximately 10-15 nm to approximately 1.0 µm and tend to be greater than 10-20 µm in length and preferably hundreds of microns in length on up to approximately 1.0 mm or more in length. The metal nanowires also advantageously exhibit high wire diameter uniformity along the length of the wire as well as from wire-to-wire for thousands of wires with a standard relative deviation from a mean diameter preferably in a range of about 5 to 20% and more preferably no more than about 10%. In addition, the metal nanowires produced by the methods of the present invention tend to be electrically continuous along their entire length, i.e., typically less than about 5% of the wires produced by the methods of the present invention tend to show any visible breaks.

The methods of the present invention include three interrelated step-decoration fabrication processes that are based on the electrodeposition of a metal or metal oxide from an aqueous solution on a basal plane-oriented surface, such as graphite, that is exposed to the solution. When suitable electric overpotentials are applied to the aqueous solution, the metal or metal oxide contained therein selectively deposits along the step edges present on the stepped surface forming "beaded-chains" of nuclei. With continued deposition, the beaded chains form three-dimensional nanowires with diameters in a range of about 10-15 nm to 1.0 µm for metal and in a range of about 20 nm to 1.3 µm for a metal oxide. The length of the nanowires tend to equal the length of the step edges on the stepped surface, which, with graphite in particular, tend to be equal to the grain diameter.

Figure 1:
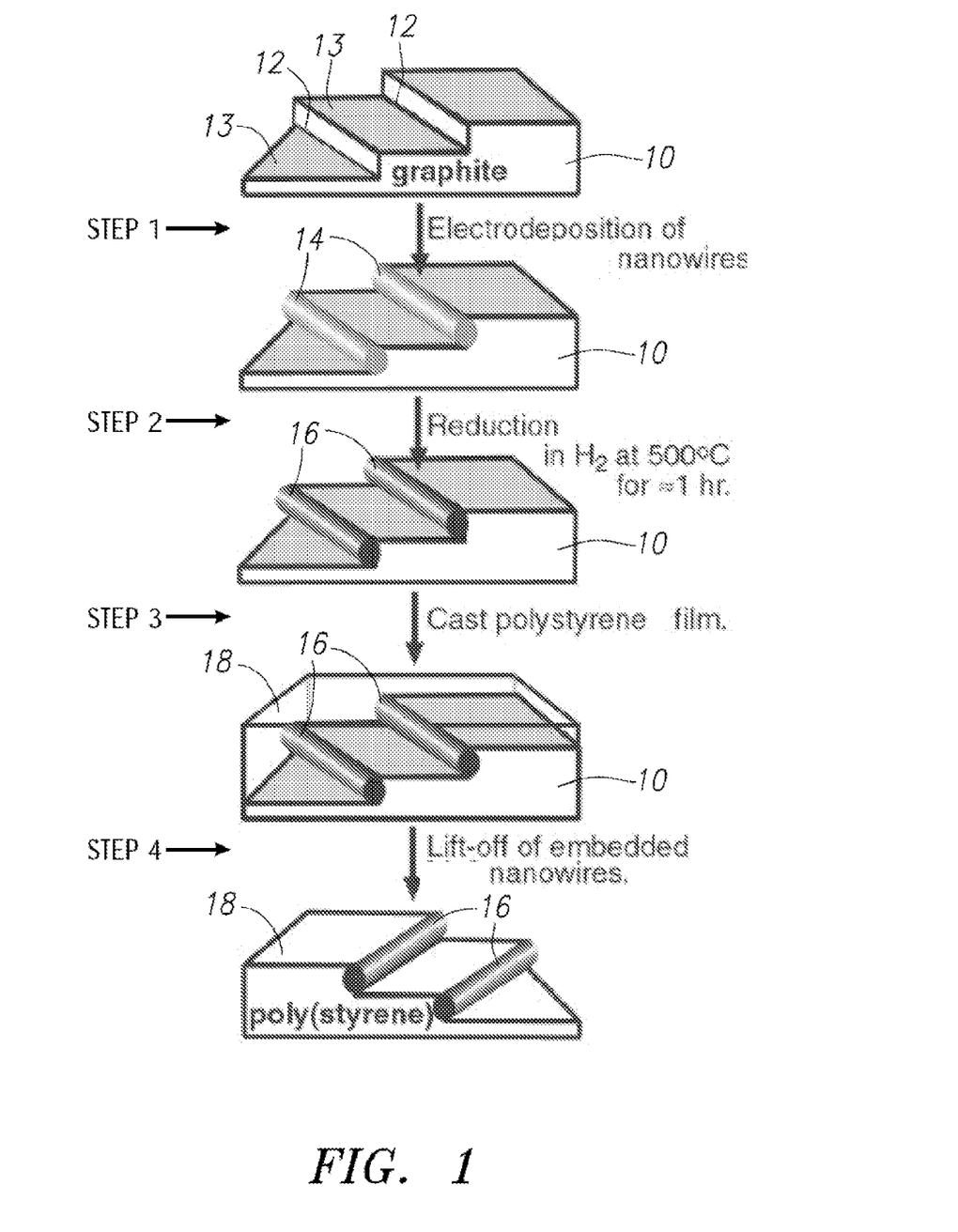
FIG. 1 is a schematic diagram of Method I of the present invention for preparing metallic nanowires.

A first embodiment of the present invention, i.e., Method I, shown schematically in FIG. 1, includes a first step (Step 1) wherein precursor nanowires 14 are selectively electrodeposited along the step edges 12 present on a stepped surface 10 from a dilute, preferably alkaline (pH of approximately 8.5), aqueous plating solution. The plating solution preferably includes an electrodepositable metal oxide at concentrations between about $1 \times 10^{-3}$ M and about $10 \times 10^{-3}$ M of the metal ion of interest. The metal oxide in the plating solution tends to nucleate at an extremely high linear density, i.e., greater than approximately 20 nuclei/micron, along the step edges 12 forming "beaded chains" of metal oxide nuclei. With continued deposition, these beaded chains rapidly become smooth, hemicylindrical precursor nanowires 14. As deposited, the precursor nanowires 14 tend to be brittle and nonconductive, but are highly uniform in diameter, with diameters in the range of about 20 nm to 1.3 µm, and tend to be hundreds of microns to about 1.0 mm or more in length.

Method I of the present invention includes a second step (Step 2) which involves a gas phase reduction of the precursor metal oxide nanowires 14 at elevated temperatures. Preferably, the metal oxide nanowires 14 are reduced in hydrogen gas ($H_2$) at about 500° C. for about one hour to produce metallic nanowires 16 that retain the dimensional uniformity and hemicylindrical shape of the precursor, or "parent", metal oxide composite nanowires 14. The metallic nanowires 16 tend to be smaller in diameter (about 10-15 nm to 1 μm) than the parent nanowires 14 by about 30 to 35%, and tend to be mechanically resilient and electronically conductive.

Figure 2:
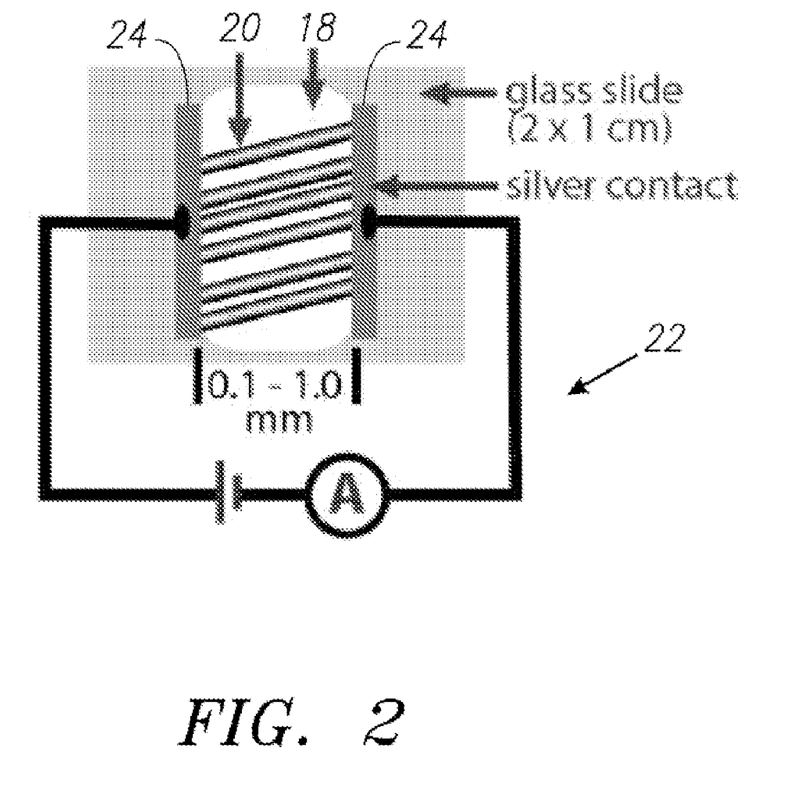
FIG. 2 is a schematic diagram of a nanometer scale electric circuit incorporating an ensemble of metallic nanowires prepared in accordance with the methods of the present invention.

In a third step (Step 3) of Method I, the gas phase reduced metal nanowires 16, which tend to be only weakly associated with the stepped surface 10, are embedded in a thin polystyrene film 18 that is cast onto the nanowires 16 and the graphite surface 10. In a fourth step (Step 4) of Method I, the film 18, after it is allowed to air dry, is peeled off of the graphite surface 10 with the metal nanowires 16 embedded therein. The embedded nanowires 16 may comprise an ensemble of tens to hundreds of nanowires or more. The ensemble of nanowires 20, which have been removed from the graphite surface 10 and, thus, are free standing, may advantageously be incorporated into an electronic circuit or sensor 22 as shown in FIG. 2. Low impedance electrical contacts 24 of silver, evaporated gold film and the like, may be connected to the ends of the nanowires 20.

Referring back to FIG. 1, the system used for electrodeposition, i.e. Step 1, preferably includes a glass electrochemical cell having a volume of approximately 50 mL. The plating solution noted above is introduced into the cell along with three electrodes: A platinum "counter" electrode, a reference electrode (e.g., saturated calomel electrode), and a "working" electrode, which is the surface, such as graphite, on which the nanowires are to be grown. The two additional electrodes—i.e., the counter and reference electrodes—enable high precision control of the potential of the working electrode. All three electrodes are preferably connected to a three-electrode potentiostat (e.g., EG&G Model 273A) which may be programmed to apply the required potential to the working electrode.

The selective decoration of the step edges 12 and, thus, wire growth, in Step 1 occurs when the deposition is carried out at suitable overpotentials, $\eta_{dep}$ (where $\eta_{dep}=E_{dep}-E_{eq}$). Suitable overpotentials, $\eta_{dep}$, used in Step 1 for wire growth may range up to about (−)900 mV versus the reversible potential[1], $E_{eq}$, of the specific material involved. If the deposition is carried out using larger overpotentials, nucleation tends to be spatially indiscriminant and metal oxide particles tend to be deposited everywhere on the surface of the step terrace 13. Moreover, if the overpotentials are too large, nucleation tends to occur on the surface of the step terrace 13 to the exclusion of the step edges 12.

The deposition process of Step 1 is preferably further characterized by the application of a constant, or nearly constant, deposition current over the deposition period, which is typically greater than 20 seconds to grow nanowires of a desired size. Preferably, the constant deposition current is in a range of about 10 to 200 microamps/cm² of electrode area. This rate invariance is consistent with a convection limited growth process where natural convective mixing of the electrolyte near an electrode surface occurs. Under these conditions the rate law for growth of a hemicylindrical solid becomes $$r(t)=(2i_{dep}t_{dep}M/\pi nF\rho L)^{1/2} \quad (1)$$

where r(t) is the radius of the hemicylindrical nanowire, $i_{dep}$ is the deposition current, $t_{dep}$ is the deposition time, M is the atomic weight of the deposited metal, n is the number of electrons transferred per metal atom, F is the Faraday constant, i.e., 96,485 C eq⁻¹, ρ is its density, and L is the total length of the nanowire(s) on the electrode surface. As indicated by Equation 1, the nanowire diameter is directly proportional to the square root of the deposition time. As a result, nanowires of a particular diameter can be selectively produced by the methods of the present invention. Further, because dr/dt is proportional to $t^{-1/2}$, the growth of highly dimensional uniform structures, i.e., populations of nanowires that are narrowly dispersed with respect to wire diameter, is possible.

As indicated above, the diameter of the precursor nanowires 14 range from about 20 nm to 1.3 μm, which is typically many times the height of the step edge 12 responsible for nucleating the growth of the wire 14. The height of the step edge 12 is typically about 0.3 to 2.0 nm. Two factors tend to contribute to this "amplification" of the step edge 12. First, at the low deposition potentials used in the methods of the present invention, the incipient nucleation sites tend to be confined to the step edges 12 on the graphite surface 10, which helps prevent the "spread" of the nanowire 14 onto terraces 13 during growth. The second factor is the inherent hemicylindrical symmetry of diffusional transport to metal nuclei arrayed along a linear step. The nanowire 14 ends up with a hemicylindrical cross-section because the ionic transport to the surface of the growing wire has this symmetry. These two factors operate in concert and permit the growth of hemicylindrical wires with virtually any diameter from step edges having molecular dimensions.

It should be understood that Method I may be used to produce metal nanowires from any conductive metal oxide that is electrodepositable, including $MoO_2$, $Cu_2O$, $Fe_2O_3$, and the like. The fabrication of molybdenum nanowires is described below with regard to FIGS. 3-5 for exemplary purposes only. See also Zach et al., Science 290 (2000) 2120[28], which is incorporated by reference as if set forth in full.

To prepare molybdenum nanowires in accordance with Method 1 shown in FIG. 1, molybdenum dioxide ($MoO_2$) is first electrodeposited (Step 1) according to the reaction:

$$MoO_4^{2-}+2H_2O+2e^-\rightarrow MoO_2+4OH^- \quad (2)$$

Figure 3:
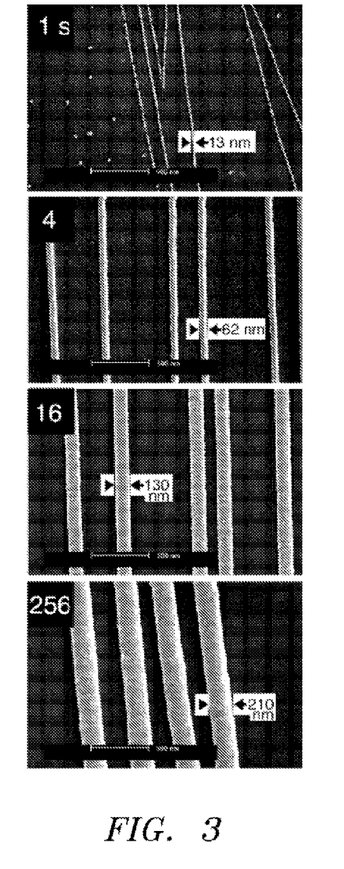
FIG. 3 is a series of scanning electron microscope images of molybdenum nanowires prepared in accordance with Method I of the present invention.

Under the conditions employed in Step 1, i.e., low overpotentials in a range of about −600 mV to −800 mV and constant, or nearly constant, deposition current in a range of about 10 to 200 microamps/cm², $MoO_2$ nucleates at an extremely high linear density (greater than about 20 nuclei/μm) along the step edges 12. The deposited $MoO_2$ forms "beaded chains" of 5-8 nm diameter $MoO_2$ nuclei which, with continued deposition, rapidly become smooth, hemicylindrical nanowires. FIG. 3 shows a series of $MoO_2$ nanowires electrodeposited according to Step I of Method 1 along step edges of a stepped graphite surface. As shown in FIG. 3, the $MoO_2$ nanowires include nanowires with diameters of 13 nm, 62 nm, 130 nm and 210 nm. The numbers at the upper left indicate the deposition time, in seconds, i.e., 1 s, 4 s, 16 s, and 256 s, for preparing these $MoO_2$ nanowires from an aqueous solution containing 1.0 mM $MoO_4^{2-}$ by applying a deposition potential of about −0.75 V vs. SCE.

Figure 4:
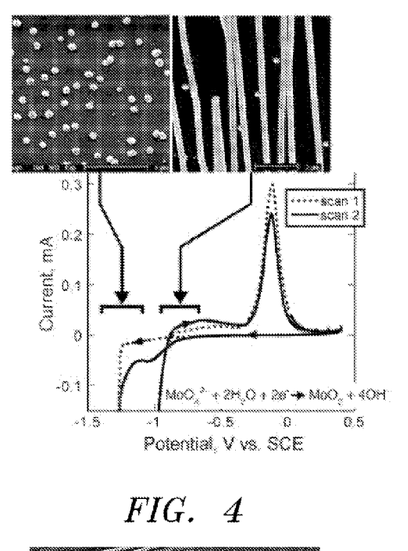
FIG. 4 is a typical cyclic voltammogram for $MoO_4^{2-}$ at a highly oriented pyrolytic graphite electrode and scanning electron microscope images (above the cyclic voltommogram) of graphite surfaces obtained following the deposition of molybdenum dioxide ($MoO_2$).

A typical cyclic voltammogram for $MoO_4^{2-}$ at a highly oriented pyrolytic graphite electrode is shown in FIG. 4. As FIG. 4 indicates, the selectivity of $MoO_2$ nucleation is controlled by the deposition potential. The scanning electron microscopy (SEM) images (above the cyclic voltammogram) of the graphite surfaces were obtained following deposition at potentials in a range of about (−)0.7 to (−)0.9 V versus a saturated calomel electrode (SCE) (right) and in a range of about (−) 1.25 to (−) 1.4 V versus SCE (left). As shown, electrodeposition of $MoO_x$, which has a reversible potential of about 0.1V, occurred with a high degree of selectivity at step edges at deposition overpotentials in the range of (−)0.6 to (−)0.8 V versus SCE (right). The application of a deposition potential more negative than (−) 1.0 V (left) caused particle growth at surface terraces.

Figure 5:
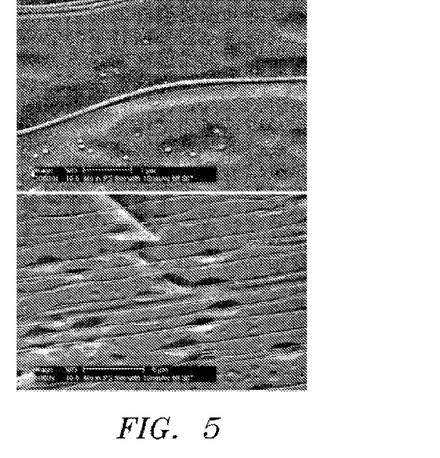
FIG. 5 includes scanning electron microscope images of molybdenum nanowires embedded in a polystyrene film after removal from a graphite surface.

Once formed, $MoO_x$ nanowires may be reduced in $H_2$ at 500° C. to produce metallic molybdenum ($Mo^0$) nanowires (Step 2). These metal nanowires are smaller in diameter by about 30% to 35% as compared with the parent $MoO_x$ wires, and are only weakly associated with the graphite surface 10. Removal of these reduced wires from the graphite surface is accomplished by embedding the nanowires in a polystyrene film (Step 3), and lifting this film together with the embedded nanowires off the graphite surface (Step 4). FIG. 5 provides SEM images of molybdenum nanowires embedded in a polystyrene film after removal from a graphite surface. The ability to remove molybdenum nanowires from the graphite surfaces on which they are synthesized facilitates the technological utility of these nanostructures both in electronic devices, as interconnects, and in sensors.

Figure 6:
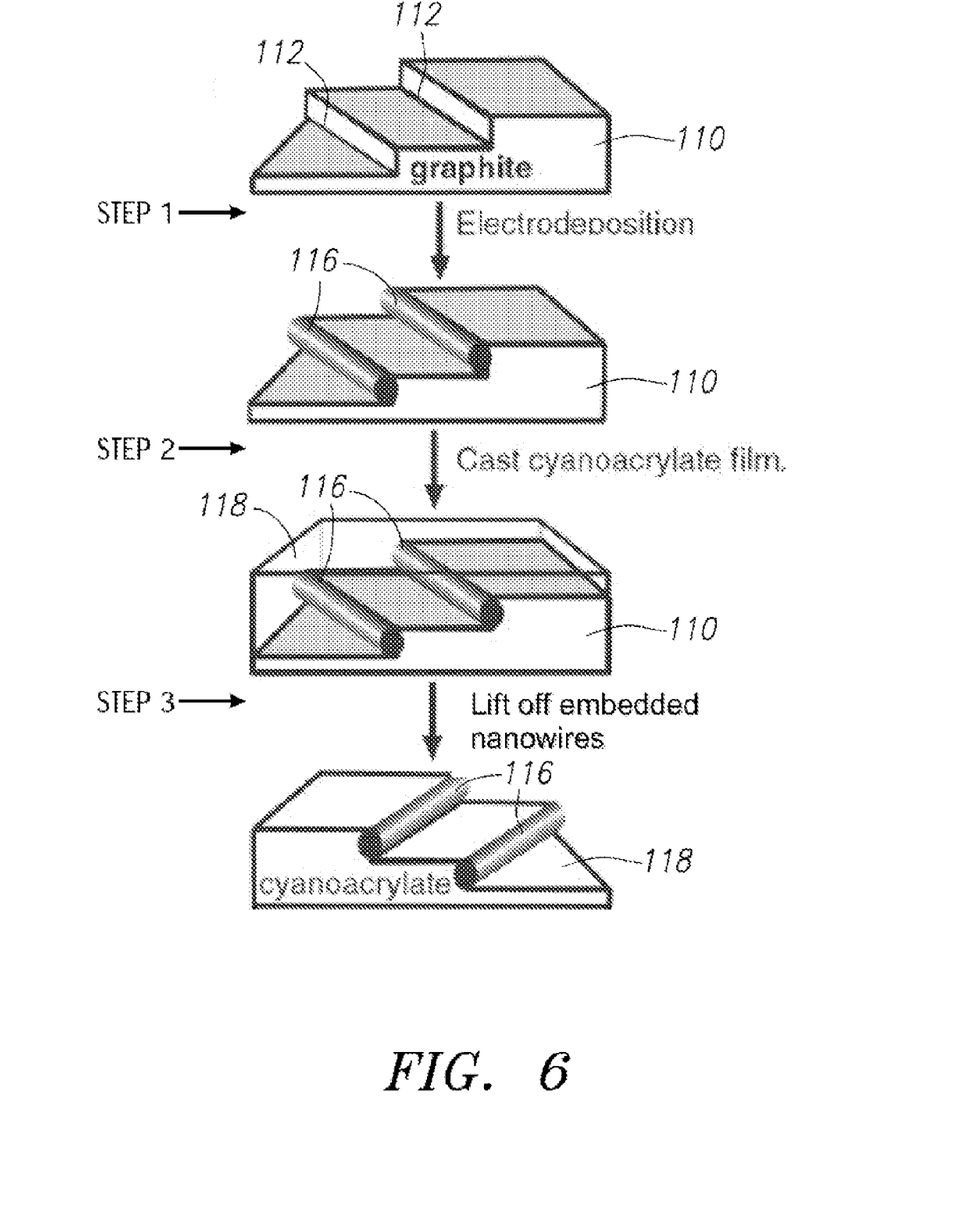
FIG. 6 is a schematic diagram of Method II of the present invention for preparing metallic nanowires by direct electrodeposition of a metal.

Turning to FIG. 6, a second embodiment of the present invention, Method II, is shown schematically to involve the preparation of metal nanowires by "direct" electrodeposition of a metal on a stepped surface 110, such as graphite, that is exposed to an aqueous solution containing the metal. In a first step (Step 1), nanowires 116 are selectively electrodeposited along the step edges 112 present on a stepped surface 110 from an aqueous plating solution comprising a electrodepositable metal. The solution preferably includes metals such as palladium, gold and the like, at concentrations between about $1\times10^{-3}$ and $10\times10^{-3}$ M of the metal ion of interest. Electrodeposition of gold, however, is preferable performed in an electrochemical cell that is pressurized to about 40 atm. Following a nucleation pulse, the metal in the plating solution nucleates at an extremely high linear density (i.e., greater than about 20/μm) along the step edges 112 forming "beaded chains" of metal nuclei, which, with continued deposition, become smooth, hemicylindrical nanowires 116.

Figure 8:
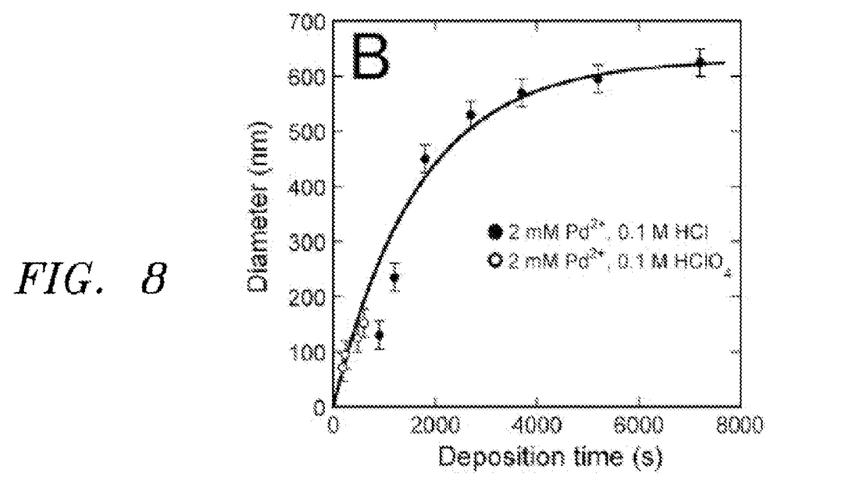
FIG. 8 is a graph showing the diameters of palladium nanowires as a function of the deposition time for nanowires deposited using the plating solutions indicated in FIG. 7.

Preferably, the electrodeposition is carried out at very low deposition overpotentials of up to about (−)400 mV and preferably in a range of about (−) 10 to (−)200 mV. To increase nucleation density and, thus, ensure that the nanowires are continuous, a nucleation pulse, well negative of the reversible potential, may be applied for about five milliseconds prior to electrodeposition at the desired overpotential. The deposition is preferably carried out at low constant, or nearly constant, deposition current, e.g., preferably less than 50 mA/cm². Depending on the metal being deposited and the applied current density, which is preferably in a range of about 5 $\mu Acm^{-2}$ to 50 $\mu Acm^{-2}$, the deposition rates in Method II are preferably extremely low. For example, as shown in FIG. 8 and discussed below, the deposition time to prepare a palladium nanowire having a 200 nm diameter was about ten minutes. Deposition rates to prepare metal nanowires of a desired diameter may be determined according to Method II may be calculated using Equation (1).

In a second step (Step 2) of Method II, the metal nanowires 116 are embedded in a thin polystyrene film 118 that is cast onto the nanowires 116 and the graphite surface 110. In a third step (Step 3), the film 118, after it is allowed to air dry, is peeled off of the graphite surface 110 with the metal nanowires 116 embedded therein. The embedded nanowires 16 may comprise an ensemble of tens to hundreds of nanowires or more. The ensemble of nanowires, which have been removed from the graphite surface 110, may also advantageously be incorporated into an electronic circuit or sensor 22 as shown in FIG. 2.

Figure 7:
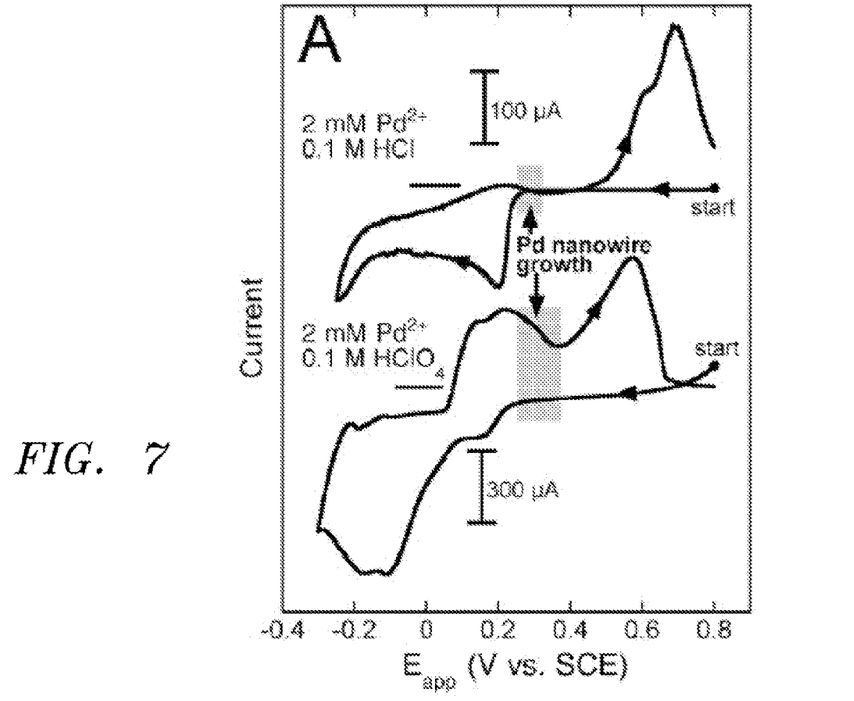
FIG. 7 includes cyclic voltommograms for a graphite electrode in two aqueous palladium plating solutions.
Figure 9:
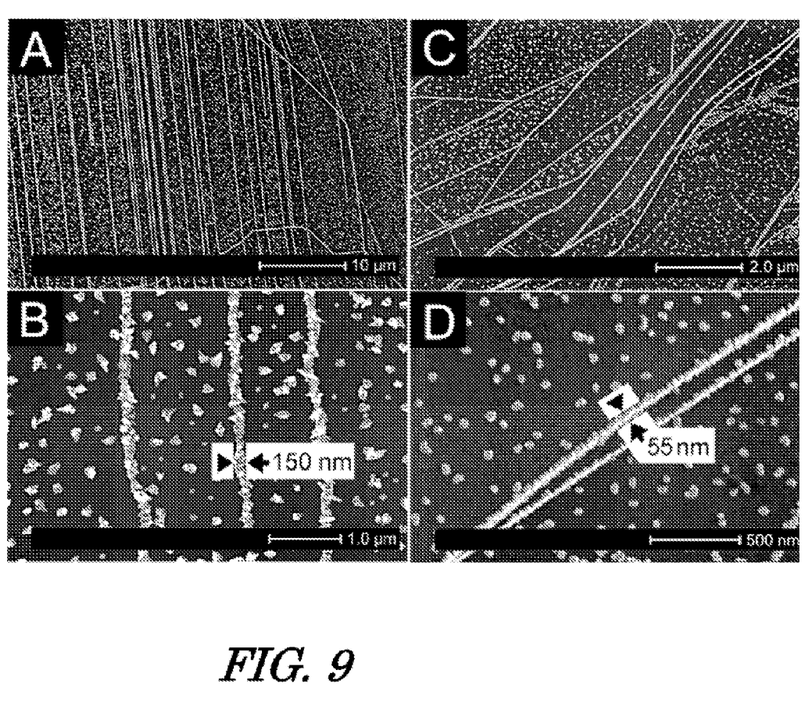
FIG. 9 includes scanning electron micrographs of palladium nanowires prepared by electrodeposition from aqueous solutions indicated in FIG. 7.
Figure 10:
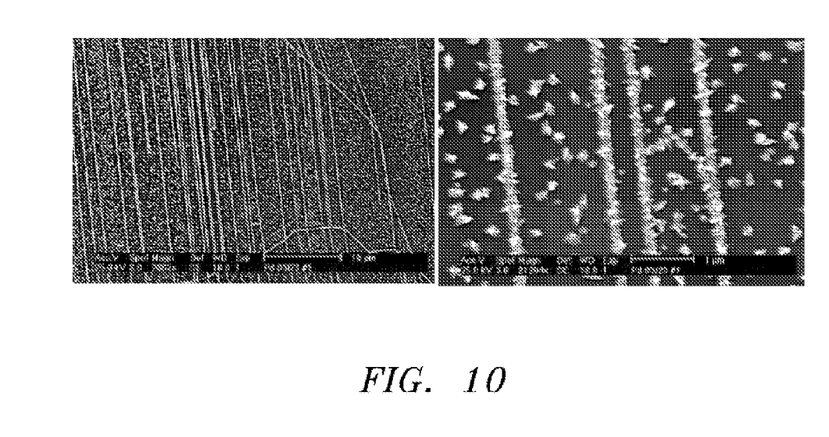
FIG. 10 includes scanning electron micrographs of 300 nanometer diameter palladium nanowires prepared in accordance with Method II of the present invention.

Palladium nanowires prepared in accordance with Method II are described in regard to FIGS. 6-10 for exemplary purposes only. Palladium nanowires may be electrodeposited from aqueous solutions containing palladium. Examples of such solutions include 2.0 mM $Pd^{2+}$, 0.1 M HCl, water, and 2.0 mM $Pd^{2+}$, 0.1 M $HClO_4$, and the like. Palladium nanowires prepared by the process of Method II are shown in FIGS. 9-10. Starting with a freshly cleaved graphite surface within a palladium plating solution, these nanowires were prepared by first applying a 5 ms nucleation pulse of −0.2 V (vs. saturated calomel electrode, SCE). As shown in FIG. 7, this potential is well negative of the reversible potential for palladium deposition in these solutions (+0.6 to +0.7 V vs. SCE). After this nucleation pulse, the growth of palladium nanowires was carried out using potentials in the ranges shown in gray in FIG. 7. These deposition potentials produce deposition current densities ranging from about 30-60 $\mu A\ cm^{-2}$ and deposition times for 200 nm diameter wires of about 10 minutes (see FIG. 8). The deposition times for palladium nanowires having 300 nm diameters, as shown in FIG. 10, were about 20 minutes.

The morphology of the palladium nanowires, as well as other metal nanowires, obtained by electrodeposition tends to be dependent on the identity of the electrolyte present in the plating solution. For example, palladium nanowires deposited from HCl solutions, as shown in FIG. 9 (left), tend to be rough and granular. The dimensions of the grains in these polycrystalline wires as estimated from SEM images ranged from about 50 to 300 nm. Continuous nanowires of 150 nm in diameter have been obtained from this solution. Deposition of palladium nanowires from $HClO_4$ solutions as shown in FIG. 9 (right), yield nanowires having a smoother morphology. The grains in these nanowires were 10-50 nm in diameter. A smoother morphology permits nanowires as narrow as 55 nm in diameter to be deposited. The rough and smooth nanowires prepared using these two plating solutions behave electrically identical to one another.

A third embodiment of the present invention, Method III, involves the preparation of beaded or hybrid metal nanowires comprising a first metal (metal A) into which nanoparticles of a second metal (metal B) have been inserted. These hybrid metal nanowires are prepared, as shown schematically in FIG. 11, by first (Step 1) electrodepositing nanoparticles 215 of metal B selectively along step edges 212 of a stepped surface 210 such as graphite. The metal B nanoparticles 215, which are preferably formed from a noble metal including nickel, palladium, platinum, gold, and the like, are electrodeposited, e.g., from an aqueous solution comprising $1.0\times10^{-3}$ m to $10\times10^{-3}$ m of the metal ion of interest using a suitable overpotential. Platinum nanoparticles, for example, are preferably deposited for 100 ms from a $1.0\times10^{-3}$ m $Pt^{2+}$ solution using an overpotential of −0.5V in order to obtain 10 nm diameter metal nanoparticles at a density of about $10^8$ to $10^{10}$ $cm^{-2}$. See, e.g., Zach et al., *Adv. Mat.*, 12 (2000) 878[29] and Zoval et al., *J. Phys. Che. B*. 102 (1998) 1166[30], and others which are incorporated by reference as if set forth in full.

Figure 11:
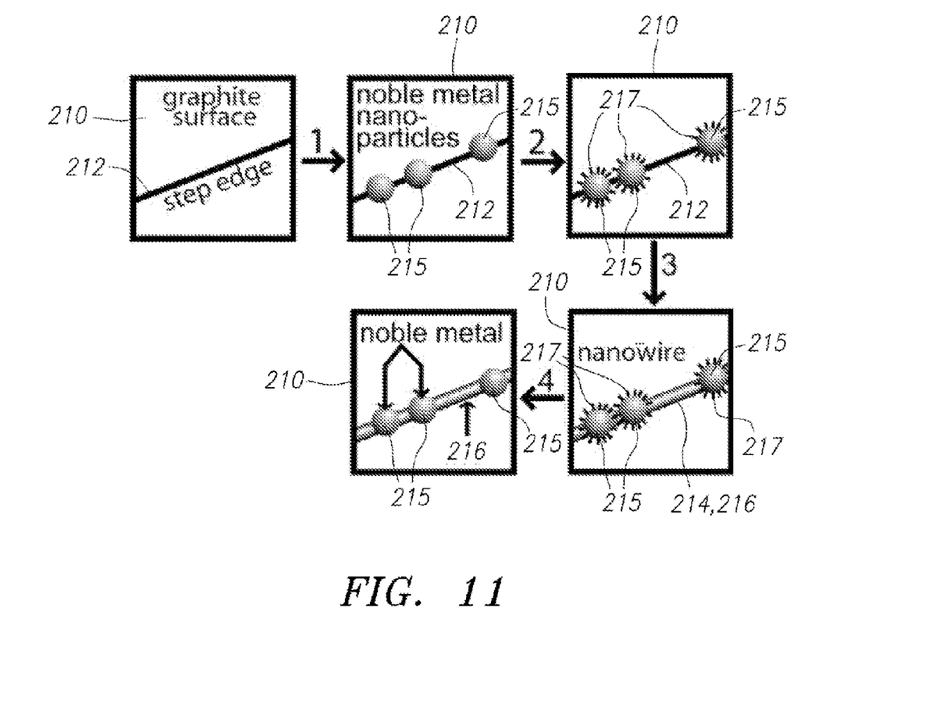
FIG. 11 is a schematic diagram of Method III of the present invention for preparing hybrid or beaded metal nanowires.

The deposited metal B nanoparticles 215 are then (Step 2) exposed to an ethanolic solution of an alkane thiol. As a result of the thiol exposure, each nanoparticle is "capped" by a self assembled molecular monolayer of an organic ligand 217 having a strong affinity for the surface of the metal B nanoparticles 215. Examples of such ligands include Thiols (chemical formula: R—SH where R is a hydrocarbon), which have an affinity for noble and coinage metals including Pt, Pd, Au, Ag, and Cu, and Nitriles (chemical formula: R—CN where R is a hydrocarbon), which have an affinity for Pt, Pd and Ag.

In a next step (Step 3), a metal A or a metal A oxide is selectively electrodeposited along the step edges 212 separating each metal B nanoparticle 215 according to Method I or II discussed above to form a metal A or metal A oxide nanowire 214, 216 between the metal B nanoparticles 215. Because the ligand 217 forms an electrically insulating layer atop of the metal nanoparticles 215, the deposition of the wire material does not occur on top of the nanoparticles 215, just between the nanoparticles 215.

Figure 12:
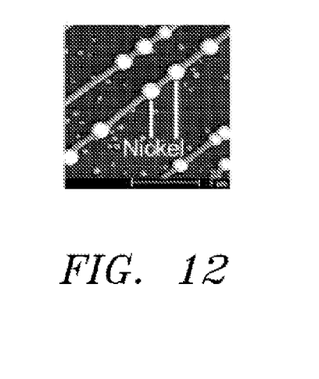
FIG. 12 is a scanning electron micrograph image of a graphite surface following the implementation of the first three steps of Method III of the present invention.

In a final step (Step 4), the ligand layer 227 is preferably removed by heating the surface under reducing conditions in order to retain the metallic composition of the particles 215 and connecting nanowire segments 216. Preferably, the reduction of the surface occurs in $H_2$ at 500° C., which results in the alkane thiol being pyrolyzed. The nanoparticles incorporated into the nanowires may range in diameter from the diameter of the nanowire itself, e.g., as small as about 10 nm, to about 1.0 μm or more. FIG. 12, which is a SEM image of a graphite surface following Step 3 of Method III, shows hybrid nanowires comprising nickel nanoparticles and molybdenum dioxide nanowire segments prepared according to Method III.

Like the metal nanowires prepared according to Methods I and II (see FIGS. 1 and 6), the hybrid nanowires prepared according to Method III may be removed from the graphite surface by embedding the wires in a polymer film, and then pealing this film containing the embedded nanowires off of the graphite surface. Because the hybrid nanowires are removable they may be utilized as elements of nanometer-scale circuits, sensors, biosensors, and the like. When used in sensors, the nanowire segments are employed to "read-out" any measurable change in the nanoparticle conductivity induced by the binding of an analyte molecule to the surface of the nanoparticle.

While the invention is susceptible to various modifications and alternative forms, specific examples thereof have been shown in the drawings and are herein described in detail. Many alterations and modifications can be made by those having ordinary skill in the art without departing from the inventive concepts contained herein. It should be understood, therefore, that the illustrated embodiments have been set forth only for the purposes of example and that they should not be taken as limiting the invention.

CITED REFERENCES

1. Bard, A. J., et al., "Electrochemical Methods, Fundamentals and Applications," 2$^{nd}$ Ed., Wiley, New York, 2001 (ISBNO-471-04372-9)
2. Behm, R. J. et al., Phys. Rev. Lett. 1999, 83 [11], 5066 [447-449, 427].
3. Himpsel, F. J. et al., Surface Review and Letters 1997, 4, 371-380.
4. Himpsel, F. J. et al., J. Mrs Bulletin 1999, 24, 20-24.
5. Kern, K. et al., Kern, K. Surf. Sci. 1998, 414, L964-L969.
6. Kern, K. et al., Phys. Rev. B 2000, 61, 2254-2262.
7. Kern, K. et al., Phys. Rev. B 2000, 61, R5133-R5136.
8. Martin, C. R. et al., Chem. Mat. 1999, 11, 1183-1185, 1185A.
9. Martin, C. R. Adv. Mat. 1991, 3, 457-459.
10. Martin, C. R. et al., Nanostructured Materials 1997, 9, 705-708.
11. Martin, C. R. et al., J. Phys. Chem. 1994, 98, 2963.
12. Martin, C. R. et al., J. Phys. Chem. 1992, 96, 9001-9007,
13. Martin, C. R. et al., J. Phys. Chem. 1992, 96, 9001.
14. Martin, C. R. et al., J. Mat. Res. 1994, 9, 1174-1183.
15. Martin, C. R. et al., J. Am. Chem. Soc. 1991, 113, 3174-3175.
16. Moskovits, M. et al, M. J. Phys. Chem. 1993, 97, 8495-8503.
17. Moskovits, M. et al, J. Phys. Chem. 1996, 100, 14037-14047.
18. Moskovits, M. et al, Phys. Rev. B 1998, 57, 13550-13553.
19. Myrick, M. L. et al., J. Electrochem. Soc. 1998, 145, 3320-3328.
20. Penner, R. M. et al., *Acc. Chem. Res.,* 33 (2000) 78.
21. Searson, P. C. et al., App. Phys. Lett. 73 (1998) 1436-1438.
22. Searson, P. C. et al., Phys. Rev. B 61 (2000) R6463-R6466
23. Searson, P. C. et al., Journal of Electronic Materials 24 (1995) 955-960.
24. Searson, P. C. et al., Science 261 (1993) 1316-1319.
25. Searson, P. C. et al., Phys. Rev. B 51 (1995) 7381-7384.
26. Searson, P. C. et al., Phys. Rev. B 58 (1998) R14681-R14684
27. Searson, P. C. et al., App. Phys. Lett. 74 (1999) 2803-2805.
28. Zach et al., *Science* 290 (2000) 2120.
29. Zach et al., *Adv. Mat.,* 12 (2000) 878.
30. Zoval et al., *J. Phys. Che. B.* 102 (1998) 1166.

What is claimed is:

1. A method for preparing a circuit comprising metallic nanometer scale wires comprising the steps of:
   providing a stepped surface comprising a common plane and step edges;
   electrodepositing a plurality of wires each comprising a chain of metal grains linearly arranged along the common plane at the step edge of the stepped surface, wherein forming the electrodepositing of wires includes linearly depositing along the common plane at the step edge of the stepped surface a beaded chain of metal nuclei, and
   forming first and second metal contacts coupled to first and second ends of the plurality of wires.

2. The method of claim 1 wherein the step of electrodepositing a plurality of wires includes applying a nucleation pulse to an aqueous solution including a desired metal.

3. The method of claim 2 wherein the step of electrodepositing a plurality of wires further includes applying a deposition potential to the aqueous solution.

4. The method of claim 3 wherein an over potential corresponding to the deposition potential is less than about −400 millivolts.

5. The method of claim 1 further comprising the step of coupling a second circuit to the first and second contacts, the second circuit comprising a power source.

6. The method of claim 1 wherein the metal grains have a diameter in the range of about 10 to 50 nanometers.

7. The method of claim 1 wherein the stepped surface comprises a basal-plane orientation.

8. The method of claim 1 wherein the stepped surface is comprised of graphite.

* * * * *